(12) United States Patent
Ziegler et al.

(10) Patent No.: US 8,365,619 B2
(45) Date of Patent: Feb. 5, 2013

(54) ASSEMBLY AND METHOD FOR EVALUATING EFFECTIVENESS OF ANTI-FOG COATINGS OF EYEWEAR LENSES

(75) Inventors: David P. Ziegler, Boxborough, MA (US); Christopher P. Drew, Clinton, MA (US); Michelle Markey, Douglas, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 81 days.

(21) Appl. No.: 12/774,458

(22) Filed: May 5, 2010

(65) Prior Publication Data

US 2011/0285997 A1    Nov. 24, 2011

Related U.S. Application Data

(60) Provisional application No. 61/215,966, filed on May 5, 2009.

(51) Int. Cl.
*G01N 17/00* (2006.01)
*G01N 21/59* (2006.01)

(52) U.S. Cl. ........................ 73/865.9; 73/865.6; 356/432

(58) Field of Classification Search .................. 73/865.9, 73/865.6; 351/41, 43, 63, 158; 128/858; 2/431; 359/512, 507
See application file for complete search history.

(56) References Cited

U.S. PATENT DOCUMENTS

| | | | |
|---|---|---|---|
| 4,815,844 A * | 3/1989 | Schmalfuss et al. | 356/239.7 |
| 5,517,700 A * | 5/1996 | Hoffman | 2/428 |
| 5,679,413 A * | 10/1997 | Petrmichl et al. | 427/534 |
| 5,712,709 A | 1/1998 | Task | |
| 6,559,939 B1 | 5/2003 | Saunders | |
| 6,780,516 B2 | 8/2004 | Chen | |
| 7,231,922 B2 * | 6/2007 | Davison et al. | 128/858 |
| 7,320,261 B1 * | 1/2008 | Hockaday et al. | 73/865.9 |
| 7,538,800 B1 | 5/2009 | Caretti | |
| 2004/0117898 A1 * | 6/2004 | Penque et al. | 2/431 |
| 2006/0238870 A1 * | 10/2006 | Sneek | 359/512 |
| 2008/0257362 A1 * | 10/2008 | Davison et al. | 128/858 |

FOREIGN PATENT DOCUMENTS

DE         4028084 A1 *   3/1992

* cited by examiner

*Primary Examiner* — Sang Nguyen
(74) *Attorney, Agent, or Firm* — Roger C. Phillips

(57) ABSTRACT

An assembly for testing the effectiveness of anti-fog coatings on eyewear lenses, the assembly comprising a chamber for receiving and retaining the eyewear, means for controlling the temperature and relative humidity in the chamber, means for providing warm moist air to the chamber, and a hazemeter for detecting and recording haze values exhibited by the lenses; and a method for evaluating effectiveness of anti-fog coatings on eyewear lenses, utilizing the assembly.

10 Claims, 1 Drawing Sheet

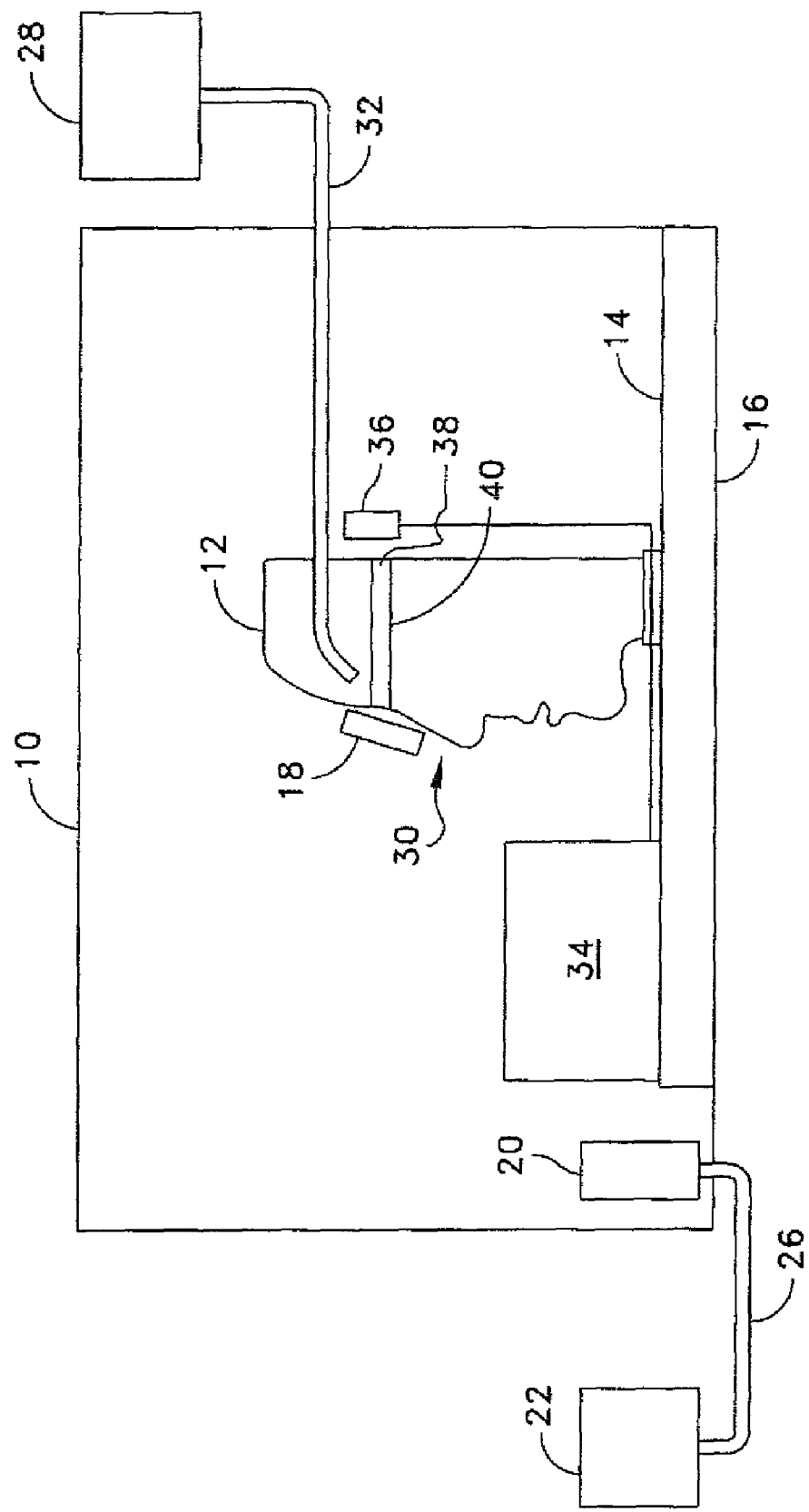

ASSEMBLY AND METHOD FOR EVALUATING EFFECTIVENESS OF ANTI-FOG COATINGS OF EYEWEAR LENSES

REFERENCE TO RELATED APPLICATION

This application claims the benefit of prior U.S. provisional Patent Application Ser. No. 61/215,966, filed May 5, 2009 by David P. Ziegler, Christopher P. Drew, and Michelle Markey.

STATEMENT OF GOVERNMENT INTEREST

The invention described herein may be manufactured and used by the United States Government for governmental purposes without the payment of any royalty thereon.

BACKGROUND OF THE INVENTION

1. Field of the Invention

The invention relates to an assembly and method for evaluating the performance and effectiveness of anti-fog products applied to eyewear lenses.

2. Description of the Prior Art

It is known to test ski goggles to measure the time for light transmission though the goggle to decrease. As condensation forms on the inner surfaces of the goggles, and scatters light passed therethrough, the light transmission through the goggles decreases.

A current test method includes placing eyewear goggles lenses horizontally on a heated water bath. A collimated laser beam is passed through the lens and a photosensor is used to measure the time for the light transmission to decrease by a selected degree as condensation forms on the inner surfaces of the lenses and scatters the light.

The test has been found wanting inasmuch as real eyewear is worn in a generally vertical position on a user's face, and the test does not account for airflow between the user's face and the eyewear frame. Further, the test does not factor in the fact that other headwear, such as hats or helmets, can interfere with airflow, and the test does not capture the dynamic nature of the fogging event.

Accordingly, there is a need for an improved test for the efficacy of anti-fog coatings on eyewear lenses.

SUMMARY OF THE INVENTION

An object of the invention is, therefore, the provision of an assembly for testing the effectiveness of anti-fog coatings applied to eyewear lenses.

A further object of the invention is the provision of a method for evaluating the effectiveness of anti-fog coatings on eyewear lenses.

In accordance with the above and other objects, there is provided herein an assembly for testing the effectiveness of anti-fog coatings applied to eyewear lenses, the assembly comprising an insulated chamber adapted to receive, support, and retain eyewear having lenses mounted thereon, the lenses having an anti-fog coating thereon, means for controlling the temperature and relative humidity of atmosphere in the chamber, means for providing a stream of warm moist air to the chamber and directed at the lenses, and a hazemeter for detecting and recording percentages of haze values over a selected period of time.

In accordance with the above and other objects, there is further provided herein a method for evaluating the effectiveness of anti-fogging coatings on eyewear lenses, the method including the steps of providing an environmentally controlled test chamber having mounted thereon eyewear having lenses with anti-fog coatings thereon, cooling the interior of the test chamber to about 10° C.-12° C., effecting a relative humidity of less that 30% in the test chamber, subjecting the rear sides of the lenses to a stream of warm moist air, and measuring per cent haze values over a selected time period.

BRIEF DESCRIPTION OF THE DRAWING

Reference is made to the accompanying drawing in which is shown an illustrative embodiment of the invention from which its novel features and advantages will be apparent.

In the drawing:

FIG. 1 is a combination block diagram and diagrammatic side view of an assembly illustrative of an embodiment of the invention.

DESCRIPTION OF THE PREFERRED EMBODIMENTS

Referring to FIG. 1, it will be seen that the assembly for evaluating the effectiveness of anti-fog coatings on eyewear lenses includes a test chamber 10 which is adapted to be closed and for the interior thereof to be environmentally controlled.

An anatomically accurate headform 12 is mounted on a bottom portion 14 of the chamber 10 which, in turn, is mounted on a supporting surface 16. The headform 12 is configured to anatomically correspond to a selected human headform such as, for example, a selected size and configuration of a human male or female, and is adapted to receive eyewear 18 similarly to the manner in which a human head receives and retains eyewear, such as spectacles, goggles, a face shield, and the like, provided with an anti-fog coating on the lens portions thereof. The headform 12 may be formed of a nylon material.

The test assembly further includes means 20 for effecting and controlling the temperature and relative humidity of the atmosphere within the chamber 10. The atmosphere preferably is maintained at a temperature of 10° C.-12° C. and a relative humidity of less than 30%. The temperature and humidity control means 20 may be a closed liquid cooling system including a chilled water circulator 22 disposed outside the chamber 20, least but communicating with the temperature and humidity control unit 20 by way of a tube 26.

The assembly further includes means 28 for providing a stream of warm moist air to the chamber 10 and, in particular, directed to the rear side of the eyewear 18, that is, between the eyewear and the headform face portion 30 by a delivery tube 32.

The assembly further includes a hazemeter 34 disposed in the chamber 10 for detecting and recording percentages of haze values over a selected period of time. Hazemeter is in communication with a detector 36 disposed adjacent a rearward opening 38 of a light transmission means 40, such as one or more tunnels extending from an area of the headform 12 behind the eyewear 18 being tested.

In an alternative embodiment, not shown in the drawings, the hazemeter may be mounted within the headform.

In operation, the headform 12 is mounted in the test chamber 10 and the test chamber is closed. The eyewear 18 to be tested is mounted on the headform 12. The atmosphere within the test chamber 10 is set and maintained at a selected temperature and humidity by the temperature and humidity control unit 20 which in supplied with chilled water from the circulator 22, by way of the tube 26.

The temperature and humidity control unit 20 is energized to maintain the atmosphere within the chamber 10 at a temperature of about 10° C.-12° C. and to maintain the relative humidity within the chamber 10 at less than 30%.

A flow of warm moist air is directed from the unit 28 to the area in the chamber 10 between the eyewear 18 and the face portion 30 of the headform 12. Thus, the rear portions of the eyewear are maintained in a warm moist condition, while the front portions of the eyewear are maintained cold and moist.

As the eyewear "fogs up", the fogging is detected by the detector 36 which is exposed to light transmission through the eyewear and through the light transmission means 40, typically a tunnel extending through the headform 12. The light detector 36 conveys light transmission data to the hazemeter 34 which stores pertinent data relative to the extent of fogging of the eyewear.

There is thus provided an assembly and method by which the benefit of an anti-fogging lens or anti-fogging coating for a lens may be tested and evaluated.

It is to be understood that the present invention is by no means limited to the particular constructions herein disclosed and/or shown in the drawing, but also comprises any modifications or equivalents within the scope of the claims.

What is claimed is:

1. An assembly for testing the effectiveness of antifog coatings applied to eyewear lenses, the assembly comprising:
   an insulated chamber adapted to receive, support, and retain eyewear having lenses mounted thereon, the lenses having an anti-fog coating thereon;
   means for controlling the temperature and relative humidity of atmosphere in said chamber;
   means for providing a stream of warm moist air to said chamber and directed at the lenses; and
   a hazemeter for detecting and recording percentages of haze values over a selected period of times; and
   further comprising an anatomically accurate headform adapted to receive eyewear, the eyewear having the lenses fixed thereon;
   wherein said means for controlling the temperature and humidity in said chamber is adapted to maintain the temperature in said chamber between 10° C. and 12° C., and to maintain the relative humidity at less than 30%.

2. The assembly in accordance with claim 1, wherein said means for controlling the temperature in said chamber comprises a liquid cooling system.

3. The assembly in accordance with claim 1, wherein said means for providing warm moist air is adapted to direct the warm moist air at sides of the lenses more proximate said headform.

4. The assembly in accordance with claim 1, wherein said hazemeter is mounted in said headform.

5. The assembly in accordance with claim 1, wherein said headform is of nylon.

6. The assembly in accordance with claim 1, wherein said headform is adapted to receive other head gear in combination with the lenses, the other head gear comprising head 1 neck and eye protection devices/ helmet mounted faceshields, air purifying respirators 1 and gas masks.

7. A method for evaluating effectiveness of anti-fog coatings on eyewear lenses, the method comprising the steps of:
   providing an environmentally controlled test chamber having mounted therein eyewear having lenses with anti-fog coating thereon;
   cooling the interior of the test chamber to about 10° C.-12° C.;
   effecting a relative humidity of less than 30% in the test chamber;
   subjecting the rear sides of the lenses to a stream of warm moist air; and
   measuring per cent haze value over a selected time period.

8. The method in accordance with claim 7 wherein the stream of warm moist air is maintained at a temperature of about 45° C. and a relative humidity of about 93% during testing.

9. The method in accordance with claim 8, wherein the haze values are measured first with no flow of warm moist air and a plurality of further values are measured at selected time intervals with flow of warm moist air, and after a last measurement the flow of warm moist air is stopped.

10. The method in accordance with claim 8 and comprising the further step of mounting a headform in the test chamber, mounting the eyewear on the headform, and directly the stream of warm moist air to an area between the lenses and the headform, and metering light transmitted through the eyewear lenses to measure a degree of haze forming on the eyewear lenses.

* * * * *